United States Patent [19]

Franz et al.

[11] 4,211,732

[45] Jul. 8, 1980

[54] N-CARBOBENZOXY-N-PHOSPHINOTHI-OYLMETHYLGLYCINE ESTERS

[75] Inventors: John E. Franz, Crestwood; Robert J. Kaufman, University City, both of Mo.

[73] Assignee: Monsanto Company, St. Louis, Mo.

[21] Appl. No.: 973,318

[22] Filed: Dec. 26, 1978

[51] Int. Cl.[1] ............................. C07F 9/40; A01N 9/36
[52] U.S. Cl. .......................................... 260/938; 71/87
[58] Field of Search ..................... 260/941, 938; 71/87

[56] References Cited

U.S. PATENT DOCUMENTS

| 3,799,758 | 3/1974 | Franz | 71/86 |
| 3,991,095 | 11/1976 | Gaertner | 71/87 |

*Primary Examiner*—Anton H. Sutto
*Attorney, Agent, or Firm*—William T. Black; Donald W. Peterson

[57] ABSTRACT

This invention relates to a new class of organic chemical compounds. More particularly, this invention is concerned with ester derivatives of N-carbobenzoxy-N-phosphinothioylmethylglycine. This class of compounds has been found to be useful as intermediates in producing N-phosphinothioylmethylglycine esters which show herbicidal activity. Some of the class of compounds of this invention also show herbicidal activity when applied to certain varieties of weeds or undesired plants.

9 Claims, No Drawings

N-CARBOBENZOXY-N-PHOSPHINOTHIOYLME-THYLCLYCINE ESTERS

This invention relates to a new class of organic chemical compounds. More particularly, this invention is concerned with ester derivatives of N-carbobenzoxy-N-phosphinothioylmethylglycine wherein ester or thioester groups are bonded to the phosphorus atom in addition to a divalent sulfur atom. Some of the members of the class of compounds have been found to display desirable herbicidal activity when applied to certain varieties of weeds or undesired plants. This class of compounds also find utility in the production of esters of N-(diester phosphinothioylmethyl)glycines by removing the N-benzyloxycarbonyl group with concentrated hydrobromic acid in acetic acid.

U.S. Pat. No. 3,799,758 describes the preparation of N-phosphonomethylglycine and certain of its esters, amides and salts. Also described is the use of such compounds as contact or post-emergent herbicides.

U.S. Pat. No. 3,991,095 describes derivatives of N-phosphonomethylglycine and salts thereof wherein there is a thiocarbonyl group attached to the nitrogen atom.

U.S. patent application Ser. No. 922,900 filed July 10, 1978 describes certain thioester derivatives of N-trifluoroacetyl-N-phosphonomethylglycine.

It will be apparent from a study of the above patents that none of them disclose or suggest phosphonomethylglycines containing a P=S grouping.

The compounds of the present invention are represented by the formula

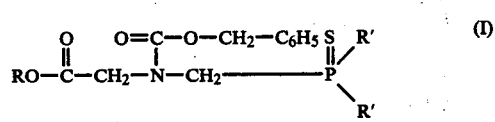

wherein R is a member of the class consisting of alkyl of from 1 to 10 carbon atoms, chloroalkyl of from 1 to 4 carbon atoms and 1 to 3 chlorine atoms, alkoxyalkyl groups containing from 3 to 9 carbon atoms and each R' is a member of the class consisting of alkoxy or thioalkyl of from 1 to 6 carbon atoms, phenoxy and phenoxy substituted with from 1 to 5 substituents selected from the class consisting of halo, methoxy and methyl, phenylthio and phenylthio substituted with from 1 to 5 substituents selected from the class consisting of halo, methoxy and methyl with the proviso that no more than one R' group can be alkoxy. It is preferred that R be alkyl of from 1 to 4 carbon atoms, and even more preferred that R represent methyl or ethyl. It is preferred that R' represent phenylthio, halophenylthio or alkylthio of from 1 to 4 carbon atoms. It is even more preferred that R' represent alkylthio of from 1 to 4 carbon atoms.

Illustrative of the alkyl groups represented by R are methyl, ethyl, n- and isopropyl, n-, sec-, iso- and tert-butyl, pentyl, hexyl, octyl and decyl. The chloroalkyl groups that R represents are, for example, chloromethyl, chloroethyl, chloropropyl, trichloropropyl, chlorobutyl and the like.

Illustrative of the alkoxyalkyl groups which R represents are methoxyethyl, methoxypropyl, methoxybutyl, ethoxyethyl, ethoxypropyl, propoxyethyl, propoxypropyl and the like.

The substituted phenoxy and phenylthio groups which R' represents are, for example, halogen-substituted groups such as chlorophenoxy, bromophenoxy, iodophenylthio, fluorophenylthio, dichlorophenylthio, dibromophenylthio, chlorobromophenoxy and the like, tolyloxy, ethylphenylthio, butylphenylthio, methoxyphenylthio, methylchlorophenoxy, ethylbromophenylthio, ethoxyphenylthio, butoxyphenoxy, and the like.

Illustrative of the alkoxy and alkylthio groups represented by R' are those alkoxy and alkylthio groups containing from 1 to 4 carbon atoms, for example, methoxy, ethoxy, isopropoxy, methylthio, propylthio, butylthio, sec-butylthio and the like.

The compounds of the present invention, i.e., compounds of formula (I), are prepared by the reaction of esters of N-carbobenzoxy-N-dichlorophosphinomethylglycine of the formula

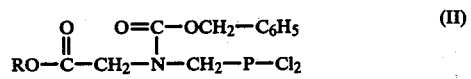

wherein R is as above defined with an alcohol or thiol of the formula

wherein R' is as above defined, in the presence of a hydrogen halide acceptor and then treating the reaction mixture with elemental sulfur.

The above reaction is generally conducted at ambient temperature. However, temperatures in the range of from 0° C. to 50° C. can be employed. Ambient temperatures of from 15° C. to 25° C. are preferred for convenience.

If it is desired to produce compounds of formula (I) wherein each R' is different, it is necessary to perform sequential steps of esterification with the hydrogen halide acceptor. In each instance, one equivalent of the compound of the formula

is added at each step.

It is, of course, apparent to those skilled in the art that for each chloro group in the compounds of formula (II) one should employ at least one equivalent of the alcohol or thioalcohol together with at least an equivalent amount of the hydrogen halide acceptor.

Inasmuch as the dichlorophosphine compounds of formula (II) are unstable towards moisture, the reaction, for best results, must be conducted in an anhydrous environment, that is, anhydrous reagents and solvents should be employed. Although the reaction can be conducted in a stepwise manner, i.e., by isolating the dichloro compound of formula (II) and then conducting the esterification and then subsequent conversion to the thioyl derivative, it is preferred for convenience to conduct the total reaction in a single reaction vessel without complete isolation and identification of the dichlorophosphinic compound.

The dichlorophosphine starting materials of formula (II) employed in the production of the compounds of this invention are prepared by the following general procedure.

An ester of N-(hydroxyphosphinylmethyl)glycine of the formula

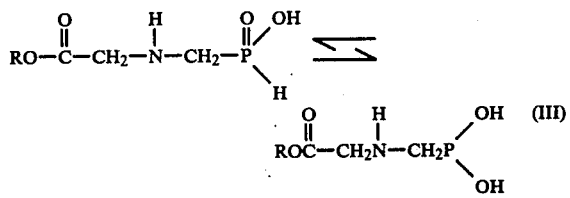

is dissolved in water cooled to 0° C. in an ice bath. An equimolar amount of benzylchloroformate and at least an equimolar amount of sodium bicarbonate is added slowly with stirring. The solution is allowed to warm to room temperature with continuous stirring. The reaction mixture is extracted with diethyl ether and the aqueous portion is adjusted to pH 2 with concentrated hydrochloric acid to precipitate the product as an oil. This oil is extracted with ethyl acetate, washed with water and dried over anhydrous sodium sulfate. After filtering, the solution is evacuated to dryness in vacuo to yield a N-benzyloxycarbonyl derivative of the formula

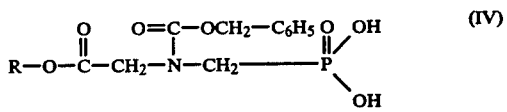

The compound of formula (IV) is then dissolved in an anhydrous aprotic solvent and treated with excess phosphorus trichloride at ambient temperatures. After filtering, the reaction mixture is concentrated in vacuo to yield the dichloro compound of formula (II).

By the term "hydrogen halide acceptor" as employed herein is meant a tertiary amine type compound such as pyridine, trimethylamine, triethylamine, tributylamine and the like.

The following examples serve to further illustrate this invention. All parts are parts by weight unless otherwise expressly set forth.

EXAMPLE 1

Ethyl-N-(benzyloxycarbonyl)-N-(hydroxyphosphinylmethyl)glycine (16.7 g., 0.0459 mole) was dissolved in 250 ml. of dry benzene and phosphorus trichloride (250 ml.) was added dropwise with stirring. The resulting solution was stirred under nitrogen for 5 minutes at room temperature and then filtered under nitrogen and concentrated in vacuo to yield a clear viscous oil. This oil was dissolved in tetrahydrofuran (100 ml.) and a solution of ethanethiol (6.26 g., 0.0918 mole) and triethylamine (10.19 g., 0.0918 mole) was added dropwise with stirring under nitrogen. The solution was stirred for an additional 2 hours and then sulfur (1.61 g., 0.0459 mole) was added and the mixture stirred overnight. The resulting suspension was filtered and concentrated to dryness in vacuo, dissolved in 100 ml. of diethyl ether and washed with a 5% aqueous sodium bicarbonate solution, 5% hydrochloric acid solution and finally with water. The ethereal solution was then dried over anhydrous magnesium sulfate, filtered and concentrated to dryness in vacuo to yield an oil. The oil was extracted with several petroleum ether washes totaling 1200 ml. The petroleum ether solutions were then concentrated to dryness in vacuo to yield ethyl-N-(benzyloxycarbonyl)-N-[bis(thioethyl)phosphinothioylmethyl]glycine as a yellow oil, $N_D^{25} = 1.5845$ and having the following analysis.

Calc'd: C, 46.88; H, 6.02; N, 3.22; P, 7.11; S, 22.08.
Found: C, 47.03; H, 6.03; N, 3.38; P, 7.15; S, 22.12.

EXAMPLE 2

Ethyl-N-(benzyloxycarbonyl)-N-(hydroxyphosphinylmethyl)glycine (6 g., 0.019 mole) was dissolved in 150 ml. of dry benzene and phosphorus trichloride (150 ml.) was added dropwise with stirring. The solution was stirred 5 minutes and then filtered under nitrogen and concentrated in vacuo to a clear viscous oil. The oil was dissolved in tetrahydrofuran (100 ml.) and a solution of benzenethiol (4.18 g., 0.038 mole) and triethylamine (3.84 g., 0.038 mole) in tetrahydrofuran (50 ml.) was added dropwise with stirring. After stirring for an additional 2 hours, sulfur (0.019 g.) was added and the suspension stirred overnight. The reaction mixture was then filtered and concentrated in vacuo, dissolved in 300 ml. of diethyl ether. The diethyl ether solution was washed with 5% aqueous sodium bicarbonate, then 5% aqueous hydrochloric acid and finally with water and then concentrated in vacuo to yield a residue. The residue was chromatographed on silica gel using benzene as the eluant to yield ethyl-N-(benzyloxycarbonyl)-N-[bis(phenylthio)phosphinothioylmethyl]glycine as a green oil, $N_D^{25} = 1.6226$ and having the following analysis.

Calc'd: C, 56.48; H, 4.93; N, 2.63; P, 5.83; S, 18.09.
Found: C, 56.36; H, 4.93; N, 2.77; P, 5.78; S, 17.90.

EXAMPLE 3

Ethyl-N-(benzyloxycarbonyl)-N-(hydroxyphosphinylmethyl)glycine (4 g., 0.0127 mole) was dissolved in dry benzene (150 ml.) and phosphorus trichloride (150 ml.) was added dropwise with stirring. The reaction was stirred for approximately 5 minutes, centrifuged and the supernatant liquid decanted from the residue which settled out. The solution was then concentrated in vacuo to dryness. The residue was dissolved in tetrahydrofuran (20 ml.) and a solution of phenol (2.39 g., 0.0254 mole) and triethylamine (2.57 g., 0.0254 mole) dissolved in tetrahydrofuran (20 ml.) was added dropwise with stirring. After stirring for an additional 1 hour, sulfur (0.406 g., 0.0127 mole) was added and the reaction stirred overnight. The reaction mixture was then filtered and concentrated in vacuo to yield an oily residue. The oily residue was extracted with petroleum ether and the petroleum ether extracts evaporated under reduced pressure to yield ethyl-N-(benzyloxycarbonyl)-N-[bis(phenoxy)phosphinothioylmethyl]glycine as an oil, $N_D^{25} = 1.5686$ and having the following analysis.

Calc'd: C, 60.11; H, 5.25; S, 6.42; N, 2.80; P, 6.20.
Found: C, 60.34; H, 5.31; S, 6.54; N, 2.70; P, 6.09.

EXAMPLE 4

Ethyl-N-(benzyloxycarbonyl)-N-(hydroxyphosphinylmethyl)glycine (6 g., 0.019 mole) was dissolved in benzene and phosphorus trichloride (20 ml.) was added dropwise with stirring. After 5 minutes additional stirring, the insoluble matter which formed in the reaction was centrifuged out and the supernatant liquid decanted and evaporated to dryness in vacuo to yield an oil. This oil was dissolved in tetrahydrofuran and a solution of methanethiol (1.82 g., 0.038 mole) and triethylamine (3.84 g., 0.038 mole) in tetrahydrofuran was added dropwise with stirring. After one hour, sulfur (0.608 g., 0.019 mole) was added and the reaction stirred overnight. The reaction mixture was then filtered and the solvents removed by evaporation under reduced pressure. The residue was dissolved in diethyl ether and the ethereal solution sequentially washed with 5% sodium bicarbonate, 5% aqueous hydrochloric acid and water. The ethereal solution was then dried over magnesium sulfate, filtered and concentrated in vacuo to yield an oil. This oil was extracted with petroleum ether and the petroleum ether extracts concentrated in vacuo to yield ethyl-N-(benzyloxycarbonyl)-N-[bis(methanethiol)-phosphinothioylmethyl]glycine as an oil, $N_D^{25} = 1.5895$ and having the following analysis.

Calc'd: C, 44.21; H, 5.44; N, 3.44; P, 7.60; S, 23.60. Found: C, 44.42; H, 5.28; N, 3.29; P, 7.40; S, 23.69.

EXAMPLE 5

Ethyl-N-(benzyloxycarbonyl)-N-(hydroxyphosphinylmethyl)-glycine (0.026 mole) was dissolved in dry benzene and added to phosphorus trichloride (approximately 10 ml.) with stirring. The reaction solution was filtered and concentrated to dryness to yield ethyl-N-(benzyloxycarbonyl)-N-[bis(chloro)phosphonomethyl]glycine. The bis-chloro compound thus obtained was dissolved in 150 ml. of tetrahydrofuran and a solution of meta-chlorophenol (6.72 g., 0.0522 mole) and triethylamine (5.27 g., 0.0522 mole) dissolved in tetrahydrofuran was added with stirring. After 90 minutes, sulfur (0.836 g., 0.0261 mole) was added and the solution stirred overnight. The reaction mixture was then filtered, concentrated in vacuo and the residue dissolved in methanol and centrifuged. The methanol solution was decanted from the precipitated sulfur and concentrated in vacuo. The residue from the methanol solution was then chromatographed on silica gel with diethyl ether as the eluant to yield ethyl-N-(benzyloxycarbonyl)-N-[bis(meta-chlorophenoxy)-phosphinothioylmethyl]glycine (3.2 g.) having the following analysis.

Calc'd: C, 52.83; H, 4.26; N, 2.46. Found: C, 52.55; H, 4.36; N, 2.39.

EXAMPLE 6

A solution of ethyl-N-(benzyloxycarbonyl)-N-(hydroxyphosphinylmethyl)glycine in benzene was added to excess phosphorus trichloride with stirring. The reaction mixture was filtered and concentrated in vacuo to yield ethyl-N-(benzyloxycarbonyl)-N-(bis-chlorophosphinomethyl)glycine. The dichloro compound (11.92 g.) thus obtained was dissolved in tetrahydrofuran and a solution of triethylaine (6.82 g.) and 2-propanethiol (5.06 g., 0.0675 mole) dissolved in tetrahydrofuran was added dropwise with stirring. The stirring was continued for one hour and then sulfur (1.05 g., 0.033 mole) was added and the reaction stirred overnight. The reaction was then filtered and the solvents removed by evaporation in vacuo. The residue was dissolved in methanol and centrifuged and the supernatant liquid concentrated to dryness to yield an oil. This oil was chromatographed on silica gel employing benzene as the eluant to yield ethyl-N-(benzyloxycarbonyl)-N-[bis(isopropyl-2-thiol)phosphinothioylmethyl]glycine as an oil, $N_D^{25} = 1.5555$ and having the following analysis.

Calc'd: C, 49.22; H, 6.52; N, 3.02; P, 6.68. Found: C, 50.34; H, 6.91; N, 2.93; P, 6.70.

EXAMPLE 7

Ethyl-N-(benzyloxycarbonyl)-N-(bis-chlorophosphonomethyl)glycine prepared as in Example 6 (9.59 g., 0.027 mole) was dissolved in tetrahydrofuran and a solution of 1-butanethiol (4.89 g., 0.0543 mole) of triethylamine (5.48 g., 0.0543 mole) dissolved in tetrahydrofuran was added dropwise with stirring. The stirring was continued for an additional hour and then sulfur (0.869 g., 0.027 mole) was added and the solution stirred overnight. The reaction mixture was then filtered and concentrated to dryness. The residue was dissolved in ether and washed sequentially with 5% aqueous sodium bicarbonate, 5% aqueous hydrochloric acid and finally with water. The ethereal solution was dried over magnesium sulfate, filtered and concentrated to dryness. The residue was dissolved in methanol, centrifuged and the supernatant methanol solution decanted and concentrated in vacuo to yield ethyl-N-(benzyloxycarbonyl)-N-[bis(1-butylthio)phosphinothioylmethyl]glycine as an oil, $N_D^{25} = 1.5471$ and having the following analysis.

Calc'd: C, 51.30; H, 6.97; N, 2.85; P, 6.30. Found: C, 51.32; H, 7.01; N, 2.90; P, 6.33.

EXAMPLE 8

Ethyl-N-(benzyloxycarbonyl)-N-(bis-chlorophosphinomethyl)glycine (13.53 g., 0.383 mole) prepared as in Example 6 was dissolved in tetrahydrofuran and a solution of isobutylthiol (6.91 g., 0.0766 mole) and triethylamine (7.74 g., 0.0766 mole) dissolved in tetrahydrofuran was added dropwise with stirring. The solution was stirred for an additional one hour period, sulfur (1.22 g.) was added and the resulting solution stirred overnight. The reaction mixture was then filtered, concentrated in vacuo and the residue dissolved in dichloromethane and washed with 5% aqueous hydrochloric acid, dried and concentrated in vacuo to yield ethyl-N-(benzyloxycarbonyl)-N-[bis(isobutylthio)phosphinothioylmethyl]glycine (16 g.) as an oil, $N_D^{25} = 1.5404$ and having the following analysis.

Calc'd: C, 49.6; H, 7.06; N, 2.74. Found: C, 50.07; H, 7.03; N, 2.81.

EXAMPLE 9

Ethyl-N-(benzyloxycarbonyl)-N-(bis-chlorophosphinomethyl)glycine (11.9 g., 0.03371 mole) prepared as in Example 6 was dissolved in tetrahydrofuran and a solution of sec-butylthiol (6.08 g., 0.0674 mole) and triethylamine (6.809 g., 0.0674 mole) dissolved in tetrahydrofuran was added dropwise with stirring. After stirring for one hour, sulfur (1.07 g.) was added and the stirring continued overnight. The reaction mixture was then filtered, concentrated to dryness in vacuo. The residue was dissolved in dichloromethane, washed with 5% aqueous hydrochloric acid and evaporated to dryness to yield ethyl-N-(benzyloxycarbonyl)-N-[bis(sec-butylthio)phosphinothioylmethyl]-glycine, $N_D^{25} = 1.5534$ and having the following analysis.

Calc'd: C, 51.30; H, 6.97; N, 2.85; P, 6.30. Found: C, 51.13; H, 6.91; N, 2.88; P, 6.42.

EXAMPLE 10

2-Chloroethyl-N-(benzyloxycarbonyl)-N-[bis(-chloro)-phosphinomethyl]glycine was prepared by reacting 2-chloroethyl-N-(benzyloxycarbonyl)-N-(hydroxyphosphinylmethyl)glycine dissolved in benzene and adding the solution to phosphorus trichloride, stirring for five minutes, filtering and evaporating to dryness in vacuo. The phosphine dichloride thus obtained (13.15 g., 0.0340 mole) was dissolved in tetrahydrofuran (100 ml.) and a solution of 2,6-dimethoxyphenol (10.48 g., 0.068 mole) and triethylamine (6.8 g., 0.068 mole) dissolved in tetrahydrofuran was added dropwise with stirring. The stirring was continued for an additional one hour after which sulfur (1.08 g., 0.0340 mole) was added. The solution was stirred overnight, filtered and concentrated in vacuo. The residue was dissolved in diethyl ether and washed three times with 3% aqueous ammonia, then once with 5% aqueous sodium bicarbonate, once with saturated aqueous sodium chloride and finally with water. The ethereal solution was then dried over magnesium sulfate, filtered and concentrated in vacuo. The residue was chromatographed on silica gel employing diethyl ether to yield 2-chloroethyl-N-(benzyloxycarbonyl)-N-[bis(2,6-dimethoxyphenoxy)phosphinothioylmethyl]glycine, hemi-hydrate as an oil, $N_D^{25}=1.564$ and having the following analysis.

Calc'd: C, 52.48; H, 5.12; N, 2.11. Found: C, 52.41; H, 5.19; N, 2.02.

EXAMPLE 11

2-Chloroethyl-N-(benzyloxycarbonyl)-N-[bis(-chloro)-phosphinomethyl]glycine prepared as in Example 10 (11.95 g., 0.0309 mole) was dissolved in tetrahydrofuran (100 ml.) and cooled to 0° C. on an ice bath. Isopropylthiol (4.69 g., 0.0618 mole) and triethylamine (6.24 g., 0.0618 mole) were dissolved in tetrahydrofuran and added dropwise with stirring to the cooled phosphine dichloride solution and stirred for one hour. Sulfur (0.989 g., 0.0309 mole) was added and the stirring continued overnight. The solution was then filtered and concentrated to dryness. The residue was dissolved in methanol and centrifuged. The supernatant methanol solution was decanted and evaporated to dryness under reduced pressure yielding an oily residue. The oily residue was dissolved in diethyl ether, washed twice with 3% aqueous ammonium hydroxide, once with saturated aqueous sodium chloride and once with 5% aqueous sodium bicarbonate solution. The ethereal solution was then dried over magnesium sulfate, filtered and concentrated in vacuo to yield 2-chloroethyl-N-(benzyloxycarbonyl)-N-[bis(isopropylthio)phosphinothioylmethyl]glycine (8.75 g.). 4 g. of this material were chromatographed on silica gel employing dichloromethane to yield 1.5 g. of the analytical sample, $N_D^{25}=1.5618$ and having the following analysis.

Calc'd: C, 45.82; H, 5.87; N, 2.81. Found: C, 46.33; H, 6.01; N, 2.94.

EXAMPLE 12

2-Chloroethyl-N-(benzyloxycarbonyl)-N-[bis(-chloro)-phosphinomethyl]glycine prepared as in Example 10 (11.9 g., 0.03078 mole) was dissolved in tetrahydrofuran (100 ml.) and cooled to 0° C. on an ice bath. Para-bromobenzenethiol (11.62 g., 0.0615 mole) and triethylamine (6.21 g., 0.0615 mole) were dissolved in tetrahydrofuran (50 ml.) and added dropwise with stirring to the cooled solution. Stirring was continued for an additional one hour after which sulfur (0.98 g., 0.03078 mole) was added. The reaction mixture was stirred overnight, filtered, and concentrated in vacuo. The residue was dissolved in dichloromethane, washed three times with 5% aqueous ammonium hydroxide, once with 5% sodium bicarbonate and once with saturated aqueous sodium chloride. The dichloromethane solution was then dried over magnesium sulfate, filtered and concentrated in vacuo to yield an oily material which are chromatographed on silica gel employing a high pressure system to yield 2-chloroethyl-N-(benzyloxycarbonyl)-N-[bis(para-bromophenylthio)phosphinothioylmethyl]glycine as an oil, $N_D^{25}=1.630$ and having the following analysis.

Calc'd: C, 41.48; H, 3.20; N, 1.93. Found: C, 42.19; N, 3.65; N, 2.00.

EXAMPLE 13

Ethyl-N-(benzyloxycarbonyl)-N-(hydroxyphosphinylmethyl)glycine was dissolved in benzene and added dropwise to a stirred solution of phosphorus trichloride to yield ethyl-N-(benzyloxycarbonyl)-N-[bis(chloro)phosphinomethyl]glycine. After stirring for 5-10 minutes, the solution was filtered and concentrated in vacuo to yield the phosphine dichloride (21.8 g, 0.0619 mole) which was dissolved in tetrahydrofuran. To the tetrahydrofuran solution was added isopropanol (3.71 g, 0.0619 mole) and triethylamine (6.255 g., 0.0619 mole) dissolved in 50 ml. of tetrahydrofuran. After stirring for one hour, thiophenol (6.86 g., 0.0619 mole) and triethylamine (6.255 g., 0.0619 mole) dissolved in 50 ml. of tetrahydrofuran was added. The reaction mixture was then stirred for two hours and sulfur (1.98 g., 0.0619 mole) was added and stirring continued overnight. The reaction mixture was then filtered, concentrated to dryness and dissolved in diethyl ether. The diethyl ether solution was then washed with 5% hydrochloric acid, 5% aqueous sodium bicarbonate and dried over magnesium sulfate. The ethereal solution was then filtered and concentrated in vacuo to yield a residue. The residue was dissolved in methanol and centrifuged to remove unreacted sulfur; the supernatant liquid was decanted and concentrated to dryness. This residue was chromatographed on silica gel employing diethyl ether as a solvent to yield ethyl-N-(benzyloxycarbonyl)-N-[(phenylthio, isopropoxy)phosphinothioylmethyl]glycine (23 g.) as an oil having a refractive index of $N_D^{25}=1.5755$ and having the following analysis.

Calc'd: C, 54.87; H, 5.79; N, 2.85. Found: C, 55.61; H, 5.77; N, 2.63.

EXAMPLE 14

Octyl-N-(benzyloxycarbonyl)-N-(hydroxyphosphinylmethyl)glycine was converted to octyl-N-(benzyloxycarbonyl)-N-[bis(chloro)phosphinomethyl]glycine by dissolving in benzene and dropwise addition to a stirred solution of excess phosphorus trichloride. After stirring for 5-10 minutes, the turbid solution was filtered and concentrated in vacuo to yield the phosphine dichloride (8.2 g., 0.0187 mole). This phosphine dichloride was dissolved in tetrahydrofuran. A solution of 2,4-dichlorophenol (3.06 g., 0.0187 mole) and triethylamine (1.89 g., 0.0187 mole) dissolved in 50 ml. of tetrahydrofuran was added to the solution of the phosphine dichloride and tetrahydrofuran. After stirring for one hour, a solution of benzylthiol (2.33 g., 0.0187 mole) and triethylamine (1.89 g., 0.0187 mole) dissolved in 50 ml. of tetrahydrofuran was then added. The reaction mixture was stirred for 2 hours and sulfur (0.601 g., 0.0187 mole) was added and stirring continued overnight. The reaction mixture was then filtered, concentrated to dryness and the residue dissolved in diethyl ether. This solution was then washed with 5% aqueous hydrochloric acid, 5% aqueous sodium bicarbonate and the ethereal solution dried over magnesium sulfate. The ethereal solution was filtered and concentrated in vacuo. The residue was then dissolved in methanol and centrifuged to remove unreacted sulfur. The supernatant methanol liquid was decanted and concentrated to dryness to yield an oily residue. The oily residue was chromatographed on silica gel to yield octyl-N-(benzyloxycarbonyl)-N-[bis(thiobenzyl, phenoxy)phosphinothioylmethyl]glycine as an oil, $N_D^{25} = 1.5672$.

EXAMPLE 15

Octyl-N-(benzyloxycarbonyl)-N-(hydroxyphosphinylmethyl)glycine was converted to octyl-N-(benzyloxycarbonyl)-N-[bis(chloro)phosphinomethyl]glycine by dissolving in benzene and adding it dropwise to a stirred solution of excess phosphorus trichloride. After stirring for 5–10 minutes, the turbid solution was filtered and concentrated in vacuo to yield the phosphine dichloride (8.5 g., 0.0194 mole). The phosphine dichloride was dissolved in tetrahydrofuran. A solution of sec-butylthiol (3.51 g., 0.0389 mole) and triethylamine (3.93 g., 0.0389 mole) dissolved in 50 ml. of tetrahydrofuran was added to the phosphine dichloride solution. The reaction was stirred for 2 hours and sulfur (0.0389 mole) was added and the stirring continued overnight. The reaction mixture was filtered, concentrated to dryness. An aliquot (500 mg.) of the residue was chromatographed on silica gel employing dichloromethane to yield octyl-N-(benzyloxycarbonyl)-N-[bis(sec-butylthio)phosphinothioylmethyl]glycine (200 mg.) as an oil having a refractive index of $N_D^{25} = 1.5247$ and the following analysis.

Calc'd: C, 56.32; H, 8.05; N, 2.43. Found: C, 56.35; H, 8.10; N, 2.40.

EXAMPLE 16

2-Ethoxyethyl-N-(benzyloxycarbonyl)-N-(hydroxyphosphinylmethyl)glycine was converted to 2-ethoxyethyl-N-(benzyloxycarbonyl)-N-[bis(chloro)phosphinomethyl]glycine by dissolving in benzene and dropwise addition to a stirred solution of excess phosphorus trichloride. After stirring for 5–10 minutes, the turbid solution was filtered and concentrated in vacuo to yield the phosphine dichloride (8.75 g., 0.022 mole). The phosphine dichloride was dissolved in tetrahydrofuran. A solution of n-butylthiol (3.97 g., 0.044 mole) and triethylamine (4.46 g., 0.044 mole) was dissolved in 50 ml. of tetrahydrofuran. The reaction mixture was then stirred for 2 hours and sulfur (0.707 g., 0.022 mole) was added and the stirring continued overnight. The reaction mixture was then filtered, concentrated to dryness and the residue dissolved in diethyl ether. The diethyl ether solution was then washed with 5% aqueous hydrochloric acid, 5% aqueous sodium bicarbonate and finally dried over magnesium sulfate. The ethereal solution was filtered and concentrated in vacuo to yield a residue. The residue was then dissolved in methanol and centrifuged to remove unreacted sulfur. The supernatant methanol liquid was decanted and concentrated to dryness to yield 2-ethoxyethyl-N-(benzyloxycarbonyl)-N-[bis(n-butylthio)-phosphinothioylmethyl]glycine (10.6 g.) as an oil, $N_D^{25} = 1.53575$ and having the following analysis.

Calc'd: C, 51.57; H, 7.15; N, 2.61. Found: C, 51.05; H, 7.13; N, 2.71.

EXAMPLE 17

Butyl-N-(benzyloxycarbonyl)-N-(hydroxyphosphinylmethyl)glycine was converted to butyl-N-(benzyloxycarbonyl)-N-[bis(chloro)phosphinomethyl]glycine by dissolving in benzene and dropwise addition to a stirred solution of excess phosphorus trichloride. After stirring for 5–10 minutes, the turbid solution was filtered and concentrated in vacuo to yield the phosphine dichloride (10.95 g., 0.0287 mole). The phosphine dichloride was dissolved in tetrahydrofuran. A solution of para-methoxyphenol (7.15 g., 0.0575 mole) and triethylamine (5.8 g., 0.0575 mole) dissolved in 100 ml. of tetrahydrofuran. The reaction mixture was then stirred for two hours and sulfur (0.921 g., 0.0287 mole) was added and the stirring continued overnight. The reaction mixture was then filtered, concentrated to dryness and the residue dissolved in diethyl ether. The diethyl ether solution was then washed with 5% hydrochloric acid, 5% aqueous sodium bicarbonate and finally dried over magnesium sulfate. The ethereal solution was then filtered and concentrated in vacuo to yield a residue. This residue was dissolved in methanol and centrifuged to remove unreacted sulfur. The supernatant methanol liquid was decanted and concentrated to dryness to yield 17.9 g. of an oily residue. The oily residue (7 g.) was chromatographed on silica gel employing dichloromethane to yield butyl-N-(benzyloxycarbonyl)-N-[bis(-para-methoxyphenoxy)phosphinothioylmethyl]-glycine (0.60 g.) as an oil, $N_D^{25} = 1.5571$ and having the following analysis.

Calc'd: C, 57.46; H, 5.6; N, 2.3 Found: C, 57.05; H, 5.90; N, 2.55.

The post-emergent herbicidal activity of some of the compounds of this invention was demonstrated by greenhouse testing in the following manner. A good grade of top soil was placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. Seeds and/or vegetative propagules were covered with soil and leveled. The pans were then placed on a sand bench in the greenhouse and watered from below as needed. After the plants had reached the desired age (two to three weeks), each pan except for the control pan was removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contained about 0.4% by weight of the emulsifier. The spray solution or suspension contained a sufficient amount of a candidate chemical in order to give application rates as indicated hereinafter. The spray solution was prepared by taking an aliquot of a 1.0% by weight stock solution or suspension of the candidate chemical in an organic solvent such as acetone or tetrahydrofuran or in water. The emulsifying agent employed was a mixture comprising 35 weight percent butylamine dodecylbenzene sulfonate and 65 weight percent of a tall oil ethylene oxide condensate having about 11 moles of ethylene oxide per mole of tall oil. The pans were returned to the greenhouse and watered as before and the injury to the plants were compared to the control and observed at approximately two or four weeks as set forth hereinafter.

In conducting this test, it was found that the compound of Example No. 1 at 11.2 kilograms per hectare gave complete control of Lambsquarters and was active against Johnsongrass and Barnyardgrass. The compound of Example No. 4 at 11.2 kilograms per hectare was active against Morningglory, Smartweed, Downy Brome and Barnyardgrass. At 11.2 kilograms per hectare, the compound of Example No. 5 was active against Barnyardgrass whereas the compound of Example No. 6 was active against Lambsquarters and Barnyardgrass. The compound of Example No. 7 was active against Morningglory and Lambsquarters at 11.2 kilograms per hectare whereas at the same rate, the compound of Example No. 8 was active against Morningglory, Smartweed and Barnyardgrass. The compound of Example No. 9 showed activity at 11.2 kilograms per hectare against Morningglory, Lambsquarters, Smartweed, Johnsongrass and Barnyardgrass. The compound of Example No. 13 at 56 kilograms per hectare showed activity against Morningglory and at 11.2 kilograms per hectare and 5.6 kilograms per hectare showed activity against Barnyardgrass. The compound of Example No. 14 at 56 kilograms per hectare showed activity against Lambsquarters. The compound of Example No. 15 at 11.2 kilograms per hectare showed activity against Canada Thistle, Lambsquarters, Smartweed, Quackgrass, Johnsongrass and Barnyardgrass. The compound of Example No. 16 at the same rate showed activity against Lambsquarters and Barnyardgrass.

The compounds of the examples can also be converted to secondary amino compounds containing these units by hydrolysis of the N-benzoyloxycarbonyl group from the nitrogen employing 35% hydrobromic acid in glacial acetic acid and then treating the hydrobromide salt obtained with propylene oxide and recovering the free secondary amine containing the N-(diester phosphinothioylmethyl)glycine carboxy ester. These secondary amine compounds are useful as post-emergent herbicides.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters of petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 11.2 to about 22.4 or more kilograms per hectare. In applications for the control of aquatic plants, the active ingredients are applied in amounts of from about 0.01 parts per million to about 1000 parts of million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

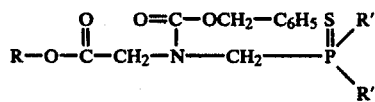

wherein R is a member of the class consisting of alkyl of from 1 to 10 carbon atoms, chloroalkyl of from 1 to 4 carbon atoms and 1 to 3 chlorine atoms, alkoxyalkyl groups containing from 3 to 9 carbon atoms and each R' is selected from the class consisting of alkoxy or alkylthio of from 1 to 6 carbon atoms, phenoxy, phenylthio and such phenoxy or phenylthio groups substituted with from 1 to 5 substituents selected from the class consisting of halo, methoxy and methyl.

2. A compound of claim 1 wherein R is an alkyl group of from 1 to 4 carbon atoms.

3. A compound of claim 2 wherein R is methyl or ethyl.

4. A compound of claim 1 wherein R' is phenylthio, halophenylthio or alkylthio of from 1 to 4 carbon atoms.

5. A compound of claim 4 wherein R' is alkylthio of from 1 to 4 carbon atoms.

6. A compound of claim 2 wherein R' is phenylthio, halophenylthio or alkylthio of from 1 to 4 carbon atoms.

7. A compound of claim 3 wherein R' is phenylthio, halophenylthio or alkylthio of from 1 to 4 carbon atoms.

8. A compound of claim 6 wherein R' is alkylthio of from 1 to 4 carbon atoms.

9. A compound of claim 7 wherein R' is methylthio or ethylthio.

* * * * *